United States Patent
Hool et al.

(10) Patent No.: US 6,770,244 B2
(45) Date of Patent: Aug. 3, 2004

(54) DIANOSTIC SAMPLE TUBE INCLUDING ANTI-ROTATION APPARATUS

(75) Inventors: Jason Dominik Hool, Pacific Palisades, CA (US); Javier Urena, San Jose, CA (US); Fredrick Spears, San Jose, CA (US); Osamu Ohno, Mountain View, CA (US)

(73) Assignee: Hitachi Chemical Diagnostic, Inc., Mountain View, CA (US)

( * ) Notice: Subject to any disclaimer, the term of this patent is extended or adjusted under 35 U.S.C. 154(b) by 445 days.

(21) Appl. No.: 09/849,860

(22) Filed: May 3, 2001

(65) Prior Publication Data

US 2002/0164270 A1 Nov. 7, 2002

(51) Int. Cl.[7] .................................................. G01N 9/30
(52) U.S. Cl. ........................ 422/72; 422/102; 422/104; 436/177; 494/16
(58) Field of Search ........................... 422/72, 99, 102, 422/104, 63, 64; 436/43, 45, 177; 494/16, 17, 20, 31, 38, 39, 41

(56) References Cited

U.S. PATENT DOCUMENTS

| | | | | |
|---|---|---|---|---|
| 4,080,175 A | * | 3/1978 | Chulay et al. ................ | 23/292 |
| 4,553,955 A | * | 11/1985 | Lam et al. .................... | 494/16 |
| 4,571,238 A | * | 2/1986 | Potter ........................... | 494/12 |
| 4,585,433 A | * | 4/1986 | Cole ............................. | 494/20 |
| 4,690,670 A | * | 9/1987 | Nielsen ........................ | 494/16 |
| 4,718,885 A | * | 1/1988 | Potter ........................... | 494/20 |
| 4,832,678 A | * | 5/1989 | Sheeran ........................ | 494/16 |
| 4,944,721 A | * | 7/1990 | Carson ......................... | 494/16 |
| 4,956,148 A | * | 9/1990 | Grandone ..................... | 422/64 |
| 5,171,531 A | * | 12/1992 | Christianson et al. ......... | 422/64 |
| 5,382,219 A | * | 1/1995 | Malekmadani ............... | 494/16 |
| 5,382,220 A | * | 1/1995 | Romanauskas et al. ....... | 494/85 |
| 5,411,465 A | * | 5/1995 | Glen et al. .................... | 494/16 |
| 5,721,141 A | * | 2/1998 | Babson et al. ................ | 436/49 |
| 5,901,873 A | * | 5/1999 | Moore .......................... | 220/669 |
| 5,935,052 A | * | 8/1999 | Hall et al. ..................... | 494/10 |
| 6,350,225 B1 | * | 2/2002 | Sheeran et al. ............... | 494/12 |

FOREIGN PATENT DOCUMENTS

WO    WO 97/43622    * 11/1997 .......... G01N/21/03

* cited by examiner

Primary Examiner—Jill Warden
Assistant Examiner—Dwayne K Handy
(74) Attorney, Agent, or Firm—Peninsula IP Group; Douglas A. Chaikin

(57) ABSTRACT

Disclosed herein is an anti-rotational apparatus for ensuring secure placement of a sample tube on a sample carousel. The sample tube includes a first open proximal end and a second closed distal end. Between the ends and located adjacent to the proximal end, the sample tube includes a radially outwardly extending annulus having an abutment surface. The abutment surface includes anti-rotational structure. The invention in an exemplary embodiment includes a sample carousel having an outer periphery zone having a plurality of openings. The openings are sized and shaped for compatible sliding engagement with the sample tube and adjacent to the openings are abutment surfaces. Each abutment surface includes anti-rotational structure and the anti-rotational structure is sized and shaped for compatible mating engagement with the sample tube anti-rotation structure.

20 Claims, 2 Drawing Sheets

DIANOSTIC SAMPLE TUBE INCLUDING ANTI-ROTATION APPARATUS

RELATED CASE INFORMATION

This case is related to U.S. patent applications, "A Diagnostic Instrument Having Overlapping Carousels", Itaya et al, Ser. No. 09/849,857 and "A Diagnostic Pipette Assembly Including Apparatus For Automated Aspiration", Hool et al, Ser. No. 09/849,731 and, filed concurrently and simultaneously with this application and for which, at this time no serial number or filing date exist.

BACKGROUND OF THE INVENTION

Field of the Invention

This invention relates generally to medical instruments and devices and methods for their use in diagnostic analysis of biological and other liquid specimens and more particularly, this invention relates to instruments and devices and methods for their use in an automated multiple simultaneous diagnostic analysis, even more particularly this invention relates to vessels for use in diagnostic situations which include structure for preventing movement between the vessel and its carrier.

In a typical diagnostic situation, a sample is taken from a patient, for example blood and placed in a container. The sample is put through various analytical procedures to assist medical personnel in diagnosing an individual's medical condition. For example, in the case of testing for a patient's allergic reaction, whole blood is taken from a patient and at least a portion of the whole blood is converted to blood serum for testing.

The blood serum is placed in a vessel, typically a cylindrical vial, having an open proximal end and closed distal end. The vessel having the sample is also known as a sample tube. The sample tube having a proximal end zone defining a sample cup for storing liquid sample. The vessel is placed on a carrier, also know as a carousel and more specifically a sample carousel. Other patient's sample are also placed on the sample carousel. Well known diagnostic instruments for analyzing such samples include another carousel, known as a diagnostic carousel, arranged in a side-by-side relationship with the sample carousel. Typically, such instruments include a separate transfer mechanism to transfer sample from the sample carousel to containers held by the diagnostic carousel. Examples of such instruments are found in US Patents such as Miyake et al, U.S. Pat. No. 6,197,255 B1 (discloses an example of side-by-side carousels which includes a liquid delivery device for removing the sample from one of the side-by-side carousels and transferring it to the other side-by-side carousel), Sasaki et al, U.S. Pat. No. 6,193,933 (also discloses similar side-by-side carousels in an automatic analysis apparatus), Mitsumaki et al, U.S. Pat. No. 5,320,966 and Wakatake, U.S. Pat. No. 5,183,638.

The containers for holding sample for diagnosis on the diagnosis carousel are known as pipettes. Each of the pipettes and the sample tubes typically include unique identifying indicia. Each pipette is matched to a unique sample tube for testing and analyzing that particular patient's serum. In the case of testing for allergy, an immunoassay is performed on the liquid sample.

The unique identifying indicia is typically machine readable and using a proper apparatus, the diagnostic instrument is able to align the pipette and the sample tube for accurate transfer of the sample to the pipette. In typical fashion, each of the carousels rotates to the alignment point because the carousels are typically rotatable. Examples of such rotatable carousels are found at Minekane, U.S. Pat. No. 4,906,433 and Berglund, U.S. Pat. No. 4,459,265 (side-by-side carousels combined with an offset platform for liquid analysis).

In practice, the unique identifying indicia must be placed on the carousel at the correct angular relationship to the machine reader or else the machine reader is unable to identify the indicia accurately and the entire process stops being automated and becomes manual. This is especially so for the sample tubes as compared with the pipettes. The sample tubes as noted above are in the shape of a cylindrical vial and easily lend themselves to rotational movement in response to the rotational forces caused by the rotation of the sample carousel.

Additionally, initial placement of the sample tubes on the sample carousel must be accurate as well. A failure to initially accurately place the sample tubes on the sample carousel will also result in misreadings or a complete stoppage of the automated process.

Additionally, as the sample carousel is handled from one location to another can also result in movement of the sample tubes relative to the sample carousel. Shaking or jostling of the carousel as it is moved onto the diagnostic instrument can easily cause the angular positioning of the unique identifying indicia to change sufficiently to cause misreadings or a complete stoppage of the automated process.

In an effort to promote correct angular positioning of the sample tubes relative to the machine reader, others have attempted various structures. For example, as shown in FIG. 1 (Prior Art), a series of samples tubes 114 is shown being carried by a sample carousel 112. The sample tubes have an annulus adjacent the open proximal end. The annulus 116 rests upon compatible structure of the sample carousel 112. It will be noted that the typical structure of the mating structures of the sample tube and carousel are provided with a generally smooth surface. Rotation of the sample tubes, a change in the angular positioning of the sample tubes relative to the sample carousel, readily takes as illustrated by arrows 120. This clearly so in response to the rotation of the sample carousel 112 as indicated by arrow 122. However, any movement of the sample carousel 112 may well cause a change in angular positioning of the sample tube relative to the sample carousel sufficient for the machine reader to be unable to correctly identify the unique identifying indicia.

Others have attempted to increase the friction between abutting surfaces of the sample tube and sample carousel by adding rubber or springs or some combination there of to the annulus surface. While these attempts probably do have some beneficial effect, it is not sufficient to ensure the type of reliability necessary for the smooth automated operation of the testing required. Additionally, such structures do not assist in the initial and correct angular placement of the sample tube on the sample carousel. And, such structures increase the cost of manufacture as a result of the additional manufacturing step to affix the rubber and/or springs.

What is needed is structure that enables a sample tube to be correctly and securely positioned on the sample carousel to avoid misreadings or a complete stoppage of the automated diagnostic process. All of this is necessary while reducing the cost of such devices.

SUMMARY OF THE INVENTION

It is an object of this invention to provide a simple and efficient structure to assist with initial and secure placement of a sample tube on a sample carousel.

It is an additional object of this invention to provide such a structure that be resistant to movement of the sample tube on the sample carousel during handling to ensure correct angular position for reading each sample tube's unique identifying indicia.

It is an additional object of this invention to provide such a structure which is both easy to use and to manufacture as well as being cost effective.

This invention is directed toward a structure for secure placement of a sample tube on a sample carousel. The sample tube includes a first open proximal end and a second closed distal end. Between the ends and located adjacent the proximal end, the sample tube includes a radially outwardly extending annulus having an abutment surface. The abutment surface includes anti-rotational structure.

The invention in an exemplary embodiment includes a sample carousel having an outer periphery zone having a plurality of openings. The openings are sized and shaped for compatible sliding engagement with the sample tube and adjacent the openings are abutment surfaces. Each abutment surface includes anti-rotational structure and the anti-rotational structure is sized and shaped for compatible mating engagement with the sample tube anti-rotation structure.

Upon engagement of the respective anti-rotational structures, the sample is secured against relative angular positioning. Thus, once the sample tube is slidably engaged with the sample carousel, there is a secure connection preventing relative angular movement of the sample tube with respect to the sample carousel. It will be appreciated that the slidable connection is not affected by the anti-rotational structure in terms of engaging and disengaging the sample tube from the sample carousel. It will also be appreciated that the anti-rotational structure assists in the initial placement of the sample tube to the sample carousel because of the secure and positive connection made between the two.

In accordance with the above objects and those that will be mentioned and will become apparent below, the anti-rotational apparatus for securing a sample tube to a carousel in accordance with this invention comprises:

a sample tube having an open proximal end and a closed distal end, the sample tube having an annulus adjacent the proximal end, the annulus being radially outwardly projecting and including an anti-rotational structure; and a carousel designed for rotation and having openings for carrying a plurality of sample tubes, at least one of the openings including compatible and mating anti-rotational structure for mating with the anti-rotational structure of the sample tube, wherein, the anti-rotational apparatus comprises the combination of the sample tube and the carousel anti-rotational structures.

In an exemplary embodiment of the sample tube includes unique identifying indicia which is machine readable. Once the sample tube is placed in the carousel, the indicia is placed at the correct angular position to be read by the machine reader. The anti-rotational apparatus as described above and more fully below, secure the indicia in angular position so that the machine makes an accurate and reliable reading of the indicia. In an additional exemplary embodiment, the indicia comprises a bar code and the machine reader comprises a bar code reader.

In still an additional exemplary embodiment, the anti-rotational structures of each of the sample tube and sample carousel comprise male and female teeth pattern. In a more detailed exemplary embodiment, the teeth patterns are mating gear teeth.

An additional preferred embodiment includes the method in accordance with this invention of securing a sample tube to a rotatable carouse for preventing movement of the sample relative to the carousel, the steps comprising:

placing a sample tube having anti-rotational structure on a carousel having compatible anti-rotational structure; and mating the anti-rotational structures of the sample tube and the carousel before rotating the carousel.

It is an advantage of this invention to a provide anti-rotational structure on the sample tube to promote secure connection of the sample tube and the sample carousel for accurate and reliable automated reading of the unique machine readable identifying indicia on the sample tube.

It is another advantage of this invention to provide such anti-rotational structure on the sample tube and carousel that promotes initial correct placement of the sample tube on the sample carousel.

It is another advantage of this invention to provide such anti-rotational structure to ensure the smooth operation of the automated diagnostic process.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 1:
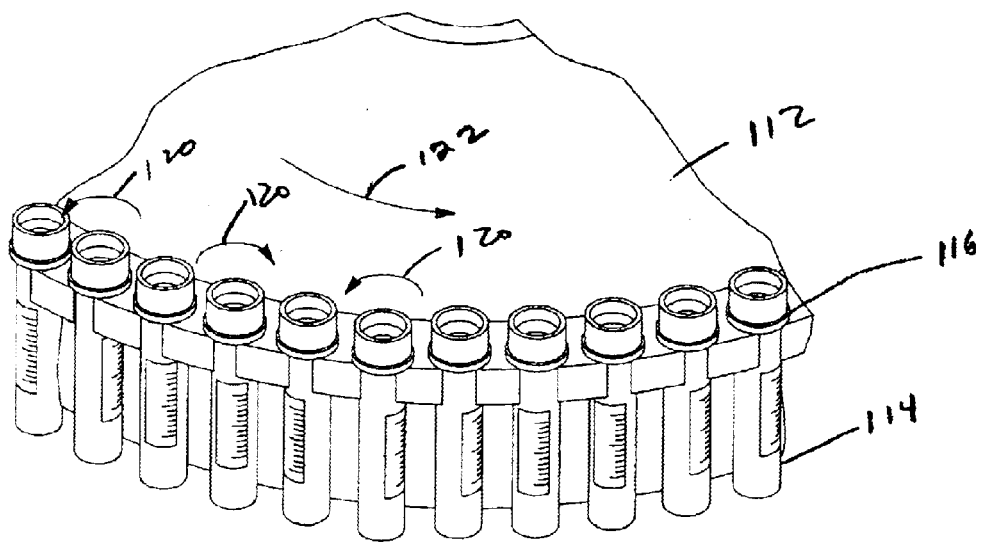
FIG. 1 is a perspective view of prior art sample tubes carried by a typical carousel.

The invention will now be described with respect to FIGS. 2–5, which illustrates a exemplary embodiment of the invention, namely, a diagnostic sample tube including anti-rotation apparatus, shown generally by the numeral 10. As shown, a carousel 12 supports and carries a sample tube 14. Unlike the prior art where the sample tube can turn relative to the carousel, the sample tube 14, in accordance with the invention, is locked in place.

The prevention of sample tube 14 movement relative to the carousel is achieved in the exemplary embodiment of the invention illustrated by the drawing, FIGS. 2–5, is a combination of the anti-rotational apparatus on the sample tube 14 and the carousel 12. With particular respect to FIGS. 2 and 3, there is shown in close up perspective view, the anti-rotational structure of the carousel. The carousel 12 has an outer zone 16 with a plurality of carrier openings 18. The outer zone openings 18 are sized and shaped for compatible engagement of the sample tube 14 and the anti-rotation structure of the sample tube 14.

Figure 3:
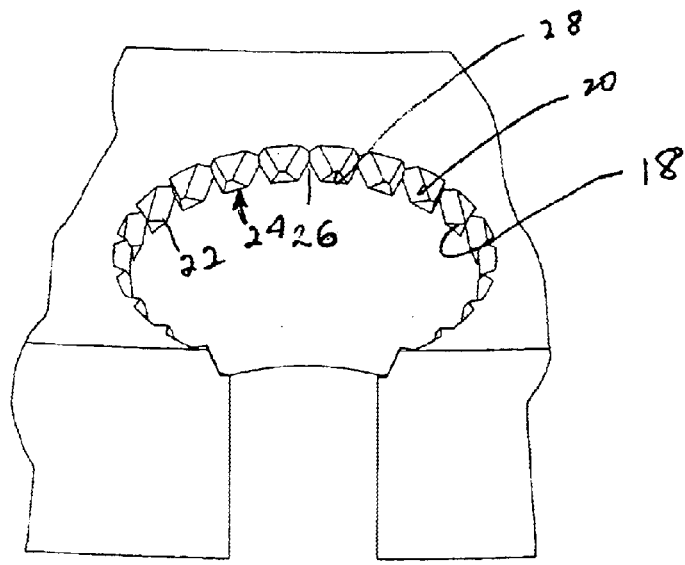
FIG. 3 is an enlarged, partially fragmentary perspective view of that portion of carousel defining the carrier having anti-rotational structure in accordance with the present invention.

In the exemplary embodiment shown in FIG. 3, the carrier openings 18 have an inner surface including anti-rotational structure 20 comprising a pattern of female teeth generally indicated by the numeral 22. The pattern includes a plurality of teeth 24 which are spaced apart. The spacing is represented by space 26 between each of the teeth 24.

The teeth rise from the inner surface in exemplary embodiment at an angle of approximately 60°. At the peak, 28, the teeth are approximately 0.86 mm wide. The spacing between the teeth is, in the exemplary embodiment, in the range of between 0.35 and 0.50 mm. Thus the space 26 varies in width in the range of between 0.35 and 0.50 mm.

Figure 2:
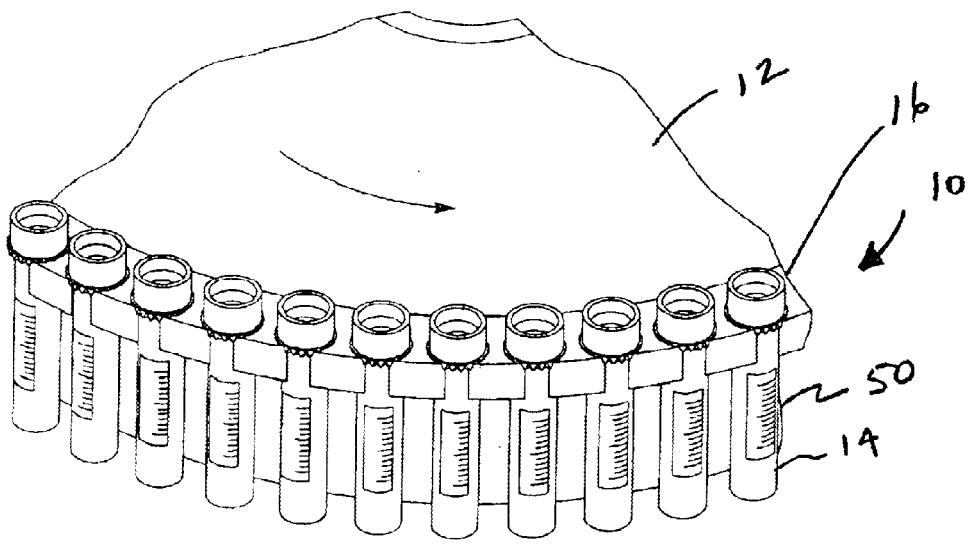
FIG. 2 illustrates, in perspective view, the anti-rotation apparatus in accordance with this invention.
Figure 4:
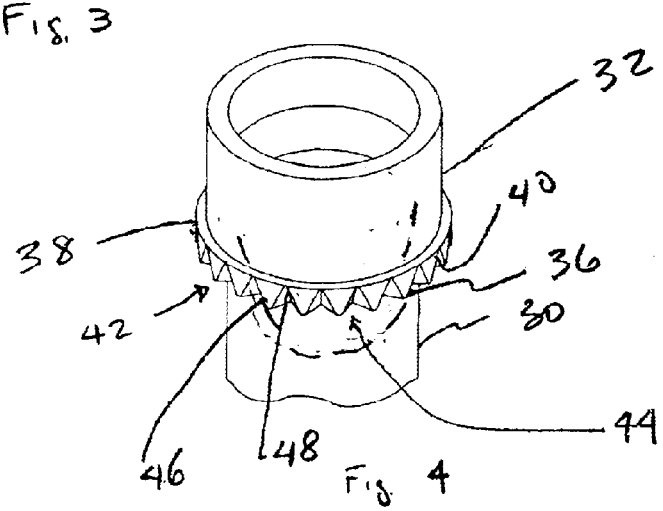
FIG. 4 is an enlarged, partially fragmentary perspective view of the sample tube also illustrating anti-rotational structure in accordance with this invention.
Figure 5:
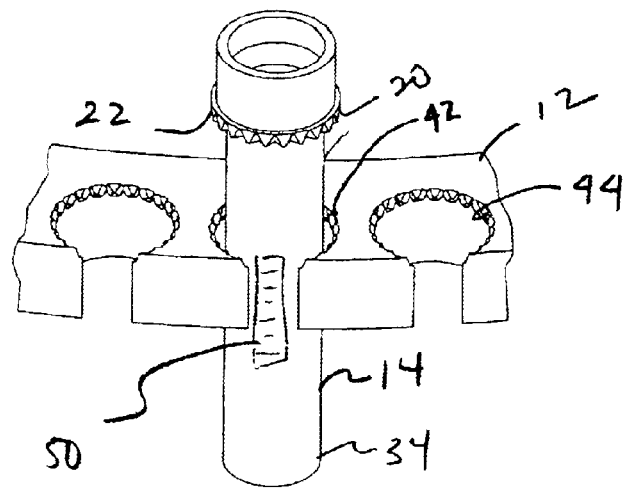
FIG. 5 is partially fragmentary perspective view of the sample tube with anti-rotational structure being connected to the carousel having compatible anti-rotational structure in accordance with the invention.

With respect to FIGS. 2, 4 and 5, there is shown the sample tube 14 in detailed enlargement. The sample tube 14 comprises a cylindrical vial 30 having a proximal end 32 and a distal end 34. The proximal end 32 is open and the distal end is closed in accordance with the sample tube of this invention. Adjacent the proximal end 32, the sample tube includes a sample cup 36, shown in phantom in FIG. 4. Sample, for example blood serum, whole blood, water or any biological fluid to be analyzed is placed in the sample cup 36.

Also, adjacent the proximal end, the sample tube has an annulus 38, extending outwardly from the sample tube 30. The annulus 38 protrudes radially from the sample tube 30. The annulus has a face 40 bearing the anti-rotation structure shown generally by the numeral 42.

The sample tube anti-rotation structure 42 is sized and shaped to be compatible with the carousel anti-rotation structure 20. As such, in the exemplary embodiment shown in FIGS. 2–5 of the sample tube anti-rotation structure 42 defines a male teeth pattern generally indicated by the numeral 44. The pattern includes a plurality of teeth 46 which are spaced apart. The spacing is represented by space 48 between each of the teeth 46.

As noted above, the teeth patterns 22 and 44 are sized and shaped to be compatible with one another. In the exemplary case illustrated in the drawing of this invention, the term compatible means to fit such that rotation is prevented, but while maintaining removable slidable engagement. In other words, the sample tube 14 is easily slid into contact with carousel 12 and just as easily removed, while rotation of the sample tube 14 relative to the carousel is prevented.

Between the sample tube proximate end 32 and the distal end 34, the sample tube includes unique identifying indicia 50 as shown in FIGS. 2 and 5. The unique identifying indicia 50 identifies this sample as belonging to one and only one patient. As explained fully in co-owned and currently co-pending US Patent Application (Unknown) filed simultaneously with the instant invention, and which is specifically incorporated herein by reference, the sample tube 14 is aligned with a pipette (not shown) so that sample can be drawn from the sample tube 14 to the pipette for testing and analysis. The pipette similarly includes unique identifying indicia and is matched with the appropriate sample tube 14.

The unique identifying indicia 50 is machine readable. In the exemplary embodiment of this invention, the machine readable indicia is read by a bar code reader (not shown). The bar code reader reads the indicia 50 recognizes the unique code and matches the unique sample tube with the appropriate diagnostic pipette for aspiration of the sample into the pipette.

As shown particularly with respect to FIG. 5, the sample tube 14 is slidably inserted into the carousel 12.

Additionally, and more particularly the indicia 50 faces outwardly, so as to afford the bar code reader an opportunity to read the indicia 50. It will be appreciated by those skilled in the art that a preferred angular position so that the bar code reader is afforded the maximum opportunity for a correct, accurate and efficient reading of the indicia 50. Thus, as best shown in FIG. 2, each of the sample tubes 14 face outwardly at the same angular position. This enables to bar code reader for the carousel to be placed and fixed for correct, accurate and efficient reading the indicia 50.

Once the anti-rotational structures of the carousel and sample tube, 20 and 42, respectively, engage one another, it is virtually impossible for the rotational movement of the carousel to dislodge the connection between them. The respective male and female teeth 46 and 24 prevent relative movement of the sample tube 14 to the carousel 12 on the mere rotation of the carousel.

However, as will be appreciated by the above description of the invention, the engagement of the teeth do not have any effect upon the slidable engagement of the sample tube 14 and the carousel 12. The teeth 46 and 24 resist movement only in the angular direction or in the exemplary case, only when the carousel rotates. Thus, while the teeth 46 and 24 provide a secure lock against movement from angular forces, they do not hinder in the least slidable contact between the sample tube 14 and the carousel 12. Once the diagnosis has been completed, the sample tubes 14 are just as easily removed from the carousel as if the anti-rotational structure had never been provided.

While the foregoing detailed description has described several exemplary embodiments of the diagnostic sample tube anti-rotational apparatus in accordance with this invention, it is to be understood that the above description is illustrative only and not limiting of the disclosed invention. Particularly, the male and female teeth may occur on either of the carousel or sample tube as long as the teeth are compatible and providing a secure structure against movement of the sample tube relative to the carousel upon the forces created by rotating the carousel. Additionally, the teeth may be larger or smaller and have different spacing without impacting the spirit or scope of this invention. It will be appreciated that the embodiments discussed above and the virtually infinite embodiments that are not mentioned could easily be within the scope and spirit of this invention. Additionally, the anti-rotational apparatus while in the exemplary embodiment is set forth as being engineering plastic, the anti-rotational apparatus may be made from whatever material is suitable for accomplishing the purposes and objectives set forth herein. These materials may include aluminum, steel, glass, and ceramic materials among others. It should also be noted that while the anti-rotation apparatus has been described with reference to circular carousels that sample tube placed in linear racks are equally susceptible to movement or jostling that can cause misalignment of the unique identifying indicia and thus the invention is specifically meant to include such linear racks as well. Thus, the invention is to be limited only by the claims as set forth below.

What is claimed is:

1. An anti-rotational apparatus for preventing rotational movement of a drop in sample tube mounted on a carousel, comprising:

a drop in sample tube having an open proximal end and a closed distal end, the drop in sample tube having an annulus adjacent the proximal end, the annulus being radially outwardly projecting and including an anti-rotational structure; and a carousel designed for receiving a drop in sample tube, the carousel being designed for rotation and having openings for carrying a plurality of sample tubes, at least one of the openings including compatible and mating anti-rotational structure for mating with the anti-rotational structure of the sample tube, wherein, the anti-rotational apparatus comprises the combination of the sample tube and the carousel anti-rotational structures.

2. The anti-rotational apparatus of claim 1, wherein the carousel plurality of openings include anti-rotational structure compatible with sample tube anti-rotational structure.

3. The anti-rotational apparatus of claim 1, wherein the carousel anti-rotational structure includes a female tooth pattern and the sample tube anti-rotational structure includes a male tooth pattern and wherein the patterns are compatible and lock each of the sample tube and carousel to each other against the forces created by rotational movement of the carousel.

4. The anti-rotational apparatus of claim 1, wherein the anti-rotational structures of the drop in sample tube and the carousel comprise gear tooth patterns, which lock each of the sample tubes and the carousel to each other against the forces created by the rotational movement of the carousel.

5. The anti-rotational apparatus of claim 1, wherein the sample tube includes unique identifying indicia between the proximal and distal ends, whereby the unique identifying indicia is held in place during rotation movement of the carousel.

6. The anti-rotational apparatus of claim 5, wherein the unique identifying indicia is machine readable.

7. The anti-rotational apparatus of claim 5, wherein the unique identifying indicia comprises a bar code and wherein the carousel is part of an overall diagnostic system which includes a bar code reader and a diagnostic pipette, the bar code reader matching sample tube to the appropriate pipette.

8. The anti-rotational apparatus of claim 1, wherein the each of the carousel anti-rotational structure and the sample tube anti-rotational structure are made from engineering plastic.

9. The anti-rotational apparatus of claim 3, wherein the tooth patterns include a series of teeth and depressions.

10. The anti-rotational apparatus of claim 9, wherein the teeth are spaced apart and the space between the teeth is in the range between 0.35 mm and 0.50 mm.

11. The anti-rotational apparatus of claim 9, wherein the teeth rise from surface at an angle of approximately 60°.

12. A diagnostic sample tube for drop in removable connection with a rotatable carousel, comprising:

a drop in cylindrical vial having a first closed end and a second open end and an outer surface extending from the first to the second end and an outwardly extending annulus protruding from the outer surface for removable connection with compatible structure on the diagnostic carousel, the annulus having a face facing toward the first end and the face having an anti-rotation apparatus; and a carousel for receiving drop in vials having an outer zone with openings compatible for removably lodging the sample tube, the outer zone having first surface facing the direction of entry of the tube with the carousel, the first surface having a anti-rotation apparatus for mating with the sample tube anti-rotation apparatus, whereby, the combination of the anti-rotation apparatus of the sample tube and carousel prevent rotation of the sample relative to the carousel upon rotation of the carousel.

13. The diagnostic sample tube as set forth in claim 12, wherein the anti-rotation apparatus includes mating male and female teeth on the anti-rotation apparatus.

14. The diagnostic sample tube as set forth in claim 13, wherein the sample tube anti-rotation apparatus has male mating teeth and the carousel has compatible female mating teeth.

15. The diagnostic sample tube as set forth in claim 12, wherein each sample tube in the carousel has a machine readable identifying indicia.

16. The diagnostic sample tube as set forth in claim 15, wherein upon mating of the anti-rotation apparatus of the corresponding sample tube and carousel, the identifying indicia is locked in proper position to be read by a machine readable device.

17. The diagnostic sample tube as set forth in claim 16, wherein the identifying indicia comprises a standard bar code and wherein a bar code reader can read the bar code.

18. A method of securing a drop in sample tube to a rotatable carousel for preventing movement of the sample tube relative to the carousel, the steps comprising:

placing a drop in sample tube having anti-rotational structure on a carousel having compatible anti-rotational structure; and mating the anti-rotational structures of the drop in sample tube and the carousel before rotating the carousel.

19. The method of claim 18, wherein the drop in sample tube is dropped into the carousel, the anti-rotational structure not interfering with the placement of the sample tube.

20. The method claim 18, wherein the carousel is rotated after the mating of the anti-rotational structures and wherein the drop in sample tube is slideably removed after rotation.

* * * * *